(12) United States Patent  (10) Patent No.: US 7,465,551 B2
Blumenthal et al.  (45) Date of Patent: *Dec. 16, 2008

(54) METHOD OF DETERMINING CYTOKINE DOSAGE FOR IMPROVING MYELOSUPPRESSIVE STATE

(75) Inventors: Rosalyn D. Blumenthal, Belleville, NJ (US); David M. Goldenberg, Mendham, NJ (US)

(73) Assignee: Center For Molecular Medicine and Immunology, Belleville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/500,186

(22) Filed: Aug. 7, 2006

(65) Prior Publication Data

US 2007/0036749 A1    Feb. 15, 2007

Related U.S. Application Data

(63) Continuation of application No. 10/173,550, filed on Jun. 14, 2002, now Pat. No. 7,112,409, which is a continuation-in-part of application No. 09/482,730, filed on Jan. 14, 2000, now Pat. No. 6,649,352.

(60) Provisional application No. 60/118,071, filed on Jan. 29, 1999.

(51) Int. Cl.
*G01N 33/53* (2006.01)
*G01N 33/567* (2006.01)
*A61K 38/19* (2006.01)

(52) U.S. Cl. .................... 435/7.1; 424/85.1
(58) Field of Classification Search .............. None
See application file for complete search history.

(56) References Cited

U.S. PATENT DOCUMENTS 7,112,409 B2 *   9/2006   Blumenthal et al. .......... 435/7.1

OTHER PUBLICATIONS

Chen et al. (1996). Japanese Journal of Clinical Oncology, 26(1), pp. 18-23.*
Chopra et al (1998). Cancer Investigation 16(3), pp. 152-159.*

* cited by examiner

*Primary Examiner*—Prema Mertz
(74) *Attorney, Agent, or Firm*—Richard A. Nakashima

(57) ABSTRACT

The invention provides kits and methods for evaluating the myelosuppressive state of a patient. These methods and kits provide a useful adjunct for cytotoxic and myelosuppressive therapies. By establishing threshold levels of certain cytokines as a surrogate for myelosuppression, treatment protocols can be optimized to reduce myelotoxicity, while maximizing effective dose. Measured levels of one or more cytokines in a patient subjected to cytotoxic therapy, relative to a normal population, may be used to determine the dose of a hematopoietic cytokine to be administered to the patient.

5 Claims, 5 Drawing Sheets

METHOD OF DETERMINING CYTOKINE DOSAGE FOR IMPROVING MYELOSUPPRESSIVE STATE

RELATED APPLICATIONS

This application is a continuation of U.S. patent application Ser. No. 10/173,550 (allowed), filed on Jun. 14, 2002, which was a continuation-in-part of U.S. patent application Ser. No. 09/482,730 (now issued U.S. Pat. No. 6,649,352), filed Jan. 14, 2000, which claimed the benefit of Provisional Application No. 60/118,071, filed Jan. 29, 1999, each hereby incorporated by reference in its entirety.

GOVERNMENT FUNDED RESEARCH

This work was supported in part by United States Public Health Service grant RO1 CA49995 (RDB) and R23 CA39841 (DMG) from the National Institutes of Health. The U.S. Government may have certain rights in the invention.

FIELD OF THE INVENTION

The present invention concerns methods and compositions for ameliorating the effects of therapy with myelosuppressive agents. In particular embodiments, the methods and compositions may allow determining the dose of a hematopoietic agent to be administered to a patient before or after myelosuppressive therapy.

BACKGROUND OF THE INVENTION

Both chemotherapy and radioimmunotherapy induce dose-limiting myelosuppression. In fact, chemotherapy-induced myelosuppression is the most common dose-limiting, and potentially fatal, complication of cancer treatment. Maxwell et al., Semin. Oncol. Nurs. 8:113-123 (1992); Blijham, Anticancer Drugs 4:527-533 (1993). Drug-induced hematopoietic toxicity is a common reason for curtailing high dose chemotherapy in cancer patients (Boesen et al., Biotherapy 6:291-302 (1993)), and higher dose chemotherapy is only possible in conjunction with bone marrow transplantation (BMT), autologous stem cell infusion, and treatment with hematopoietic growth factors.

During the recovery period after anticancer myelosuppressive therapy, hematopoietic progenitor cells become mitotically active in order to replenish the marrow compartment and remain hyperproliferative even after normalization of peripheral white blood cells (pWBCs) and platelets (PLTs). At this stage, the progenitors are more radio- and chemo-sensitive. Dosing patients with additional cytotoxic therapy during this phase will likely result in more severe toxicity.

As a general model of myelosuppressive therapy, acute damage and recovery of hematopoietic stem and precursor cells following whole-body irradiation also has been studied extensively. Testa et al., Anticancer Res. 5:101-110 (1985); Sado et al., Int. J. Radiat Biol 53:177-187 (1988); Meijne et al., Exp. Hematol. 19:617-623 (1991). External beam irradiation results in long-term damage of hematopoietic stem cells, which manifests with the presence, but at sub-optimal levels, of mitotically active, hematopoietic progenitor cells (CFU-S) 3-6 months after treatment. Lorimore et al., Int. J. Radiat Biol 57:385-393 (1990); Lord et al., Int. J. Radat. Biol. 59:211-218 (1991). Persistent depletion of femoral and splenic CFU-S (colony forming unit-spleen), CFU-GM (colony forming unit-granulocytic-monocytic) and BFU-E (burst forming unit-erythroid) can occur, even though the peripheral blood contains normal cell numbers. Grande et al., Int. J. Radiat. Biol. 59:59-67 (1993). Severe reduction in the supportive stroma has also been reported. Tavassoli et al., Exp. Hematol. 10:435-443 (1992). Following radiation exposure, recovery proceeds by repair of sublethal cellular injury and compensatory cellular repopulation by the surviving fraction. Hall in RADIOBIOLOGY FOR THE RADIOBIOLOGIST (Harper & Row 1978); Jones et al., Radiation Res. 128:256-266 (1991).

Normal white blood cell (WBC; >4000/mm$^3$) and platelet (PLT; >100,000/mm$^3$) counts are the usual markers for patient tolerance to repetitive myelosuppressive treatment. However, preclinical and clinical evidence suggests that peripheral counts are not a reliable surrogate for predicting complete myelosuppressive recovery. Although WBC and PLT counts may appear normal, the primitive stem and progenitor cell compartments are not fully recovered from previous myelosuppressive therapy.

Further cytotoxic treatment while stem cells and progenitor cells are rapidly proliferating can result in more severe myelotoxicity or even death. One solution to this problem is to collect bone marrow (BM) aspirates and use a long-term culture system to quantitate high proliferative potential CFC (HPP-CFC) or long term culture initiating cells (LTC-IC). Eaves et al, Tiss. Culture Meth. 13:55-62 (1991); McNiece et al., Blood 75:609-612 (1989). While this method can provide the needed information, such assays take 3-6 weeks to perform, and thus are not clinically useful.

During hematopoiesis, pluripotent stem cells differentiate and proliferate in multiple lineages. The process proceeds under the permissive influence of "early" and "late" hematopoietic cytokines. Lowry et al., J. Cell Biochem. 58:410-415 (1995). "Early" stimulatory factors include SCF, FLT-3-L, IL-1, IL-3, IL-6, and IL-11. In addition to these positive regulators, hematopoiesis is also controlled by inhibitory cytokines. Negative regulation of myelopoiesis occurs through several inhibitory cytokines, most notably MIP-1α (Cooper et al., Expt. Hematol. 22:186-193 (1994); Dunlop et al., Blood 79:2221-2225 (1992)), TGFβ3 (Jacobsen et al., Blood 78:2239-2247 (1991); Maze et al., J. Immunol. 149:1004-1009 (1992)) and TNFα (Mayani et al., Eur. J. Haematol. 49:225-233 (1992)).

Thus far a temporal change in these inhibitory peptides as a function of time after cytotoxic therapy has not been quantitated. It is known, however, that under stressful conditions, such as irradiation, chemotherapy, blood loss, infection or inflammation, both stimulatory and inhibitory growth factors play a major role in cellular adaptation processes. Cannistra et al., Semin. Hematol. 25:173-188 (1988). Under stress, the quiescent CFU-S component of the stem cell compartment is triggered into active cell cycling and returns to the predominantly $G_0G_1$ phase once normal bone marrow cellularity is restored. Becker et al., Blood 26:296-304 (1965).

The recent literature has highlighted several important areas where a noninvasive method to monitor myelorecovery could have considerable clinical benefit. For example, to improve the safety and cost effectiveness of high-dose regimens, hematopoietic cell support (cytokines) has been used to accelerate marrow recovery following myeloablative therapy. This approach results in an earlier recovery of peripheral blood counts, but the proliferative status of the marrow remains unknown and could be in a very active and sensitive state.

Another relevant example pertains to the use of allogeneic or autologous BMT, or more recently peripheral stem cell transplantation (SCT) following myelosuppressive or myeloablative therapy. Under those conditions, hematopoiesis is characterized by a prolonged and severe deficiency of marrow progenitors for several years, especially of the erythroid and megakaryocyte types, while the peripheral WBCs and PLTs have reached relatively normal values within a few weeks. Therefore, successful engraftment can not be measured by normalization of WBCs or PLTs, but requires another type of marker, perhaps one associated with normal marrow stromal function. Domensch et al., Blood 85:3320-3327 (1995). More information is needed to determine 'true' myelorecovery when either BMT or SCT is utilized. Talmadge et al., Bone Marrow Transplant. 19(2):161-172 (1997).

Yet another area where a noninvasive measure of myelorecovery may be useful is for scheduling leukapheresis. Since patient-to-patient variability in time to marrow recovery is quite variable following G-CSF stem cell mobilization, it is difficult to predict the best time for this procedure. Identification of one or more markers of myelotoxic nadir and recovery could advance SCT technology. Shpall et al, Cancer Treat. Res. 77:143-157 (1997).

One investigator has shown that after allogeneic or autologous BMT, a rise in endogenous G-CSF levels precedes and correlates with myeloid engraftment. Cairo et al., Blood 79(7):1869-1873 (1992). Moreover, in patients suffering from acute bacterial infections, whose rate of myelopoiesis must adapt to the enhanced demand, G-CSF, but not GM-CSF, was elevated. Selig et al., Blood 79:1869-1873 (1995). Additional studies demonstrated that the stem cell subset responsible for reconstitution is responsive to GM-CSF, IL-3, IL-6, and SCF. Wagemaker et al., Stem Cells 13:165-171 (1995). Other reports have quantified one or more cytokines during a myelosuppressive episode. Sallerfors et al., Br. J. Hematol. 78:343-351 (1991); Baiocchi et al., Cancer Research 51:1297-1303 (1996); Chen et al., Jap. J. Clin. Oncol. 26:18-23 (1996). Heretofore, however, no one carefully studied the recovery phase following myelosuppression, and there exists no correlation with the ability to redose without severe toxicity. A relatively new stromal cell-produced positive stimulatory cytokine, FLT-3-L (Brasel et al., Blood 88:2004-2012 (1996); Lisovsky et al., Blood 88(10):3987-97 (1996)), has not been studied at all to date regarding either constitutive or induced hematopoiesis. The ability to predict the magnitude of myelotoxicity in response to a given dose of RAIT would permit patient-specific dosing. Red marrow absorbed doses have not been highly predictive of hematopoietic toxicity in RAIT-treated patients. DeNardo G L, DeNardo S J, Macey D J, Shen S, Kroger L A. Overview of radiation myelotoxicity secondary to radioimmunotherapy using $^{131}$I-Lym-1 as a model. Cancer. 1994; 73:1038-1048. Juweid M E, Zhang C, Blumenthal R D, Hajjar G, Sharkey R M, Goldenberg D M. Prediction of hematologic toxicity after radioimmunotherapy with $^{131}$I-labeled anticarcinoembryonic antigen monoclonal antibodies. J Nucl Med. 1999; 40:1609-1616.

Although the dose-toxicity relationship is likely to improve as more patient-specific models for the calculation of red marrow dose are implemented, more work needs to be done to define the tolerance of patients who have received therapy prior to nonmyeloablative radioimmunotherapy (RAIT). Thus, methods need to be established that reflect more accurately the marrow reserve in patients, so that the activity prescription for RAIT can be adjusted accordingly.

In previous work (Blumenthal R D, Lew W, Juweid M, Alisauskas R, Ying Z, Goldenberg D M. Plasma FLT3-L levels predict bone marrow recovery from myelosuppressive therapy. Cancer. 2000; 88:333-343), it was demonstrated that 13% of the patient population studied experienced significantly less toxicity than was predicted by their marrow dose and 15% of the same population experienced significantly greater toxicity than predicted. Many of these patients have received multiple treatments of external beam radiation therapy and/or chemotherapy prior to receiving RAIT. It was postulated that long-term hematopoietic damage from prior cytotoxic therapy might render a patient's marrow more "brittle" and therefore more radiosensitive to the RAIT dose. Additional tumor-produced cytokines may also be a significant factor influencing the proliferation rate of marrow cells, thereby affecting their response to radiation from RAIT. R. D. Blumenthal, A. Reising, E. Leon, and D. M. Goldenberg. Modulation of marrow proliferation and chemosensitivity by tumor-produced cytokines from syngeneic pancreatic tumor lines. American Society of Hematology Annual Meeting Abstracts, 2001; #946.

FLT3-L is a growth factor involved in early hematopoiesis, is expressed in transmembrane and soluble forms, and stimulates/co-stimulates proliferation and colony formation of hematopoietic myeloid and lymphoid stem/progenitor cells (CFU-GM and CFU-GEMM) in bone marrow, spleen and peripheral blood. Lisovsky M, Braun S E, Ge Y, et al. Flt3-ligand production by human bone marrow stromal cells. Leukemia. 1996; 10:1012-1018. Brasel K, McKenna H J, Morrissey P J, et al. Hematological effects of flt3-Ligand in vivo in mice. Blood. 1996; 88:2004-2012. Papayannopoulou T, Nakamoto B, Andrews R G, et al. In vivo effects of flt3/flk2-ligand on mobilization of hematopoietic progenitors in primates and potent synergistic enhancement with granulocyte colony-stimulating factor. Blood. 1997; 90:620-629. By itself, FLT3-L has weak colony-stimulating activity, but is additive to greater-than-additive on colony number and size when combined with other colony stimulating factors (CSFs). In addition, a need still exists to establish a predictive marker for a sizeable number of individuals who experience significantly less toxicity for a given marrow dose of RAIT, than was expected.

Therefore, a need exists in the art for improved methods, and kits for implementing them, for predicting myelosuppressive recovery in conjunction with the foregoing deficient therapeutic techniques. Such methods could be used to help optimize treatment, informing the clinician of the appropriate timing of treatment, especially retreatment, thus avoiding toxic effects, while maximizing efficacious ones. Provided such a method, the art would posses new, optimized methods of treatment.

SUMMARY OF THE INVENTION

It is therefore an object of the invention to provide kits and methods for evaluating the myelosuppressive state of a patient. According to this object, the invention provides a kit which contains at least one cytokine-specific detection reagent that is adapted to detect a threshold level of a cytokine, which correlates with the myelosuppressive state. In one embodiment, the cytokine-specific reagent is specific for FLT3-L, TNF-α or TGF-β, and the reagent may comprise an antibody or antibody fragment.

Also according to this object of the invention, a method of assessing the myelosuppressive state of a patient is provided. This method entails comparing the amount of at least one cytokine in a patient sample with a threshold level, thereby gauging the myelosuppressive state of the patient. In one embodiment, the cytokine specific reagent is specific for FLT3-L, TNF-α or TGF-β, and the reagent may comprise an antibody or antibody fragment.

It is another object of the invention to provide an improved method of treating cancer or any disease when using bone-marrow suppressive agents. Further to this object, a method is provided where a patient is administered an effective amount of an anti-cancer or other cytotoxic agent and the level of at least one cytokine is compared with a threshold level. In one embodiment, the cytokine is FLT3-L, TNF-α or TGF-β. In other aspects, the method involves using the threshold level to guide treatment, so that when the threshold is approached or crossed, treatment is halted or decreased until it is no longer approached or exceeded

DETAILED DESCRIPTION OF THE INVENTION

A. Definitions

Figure 1:
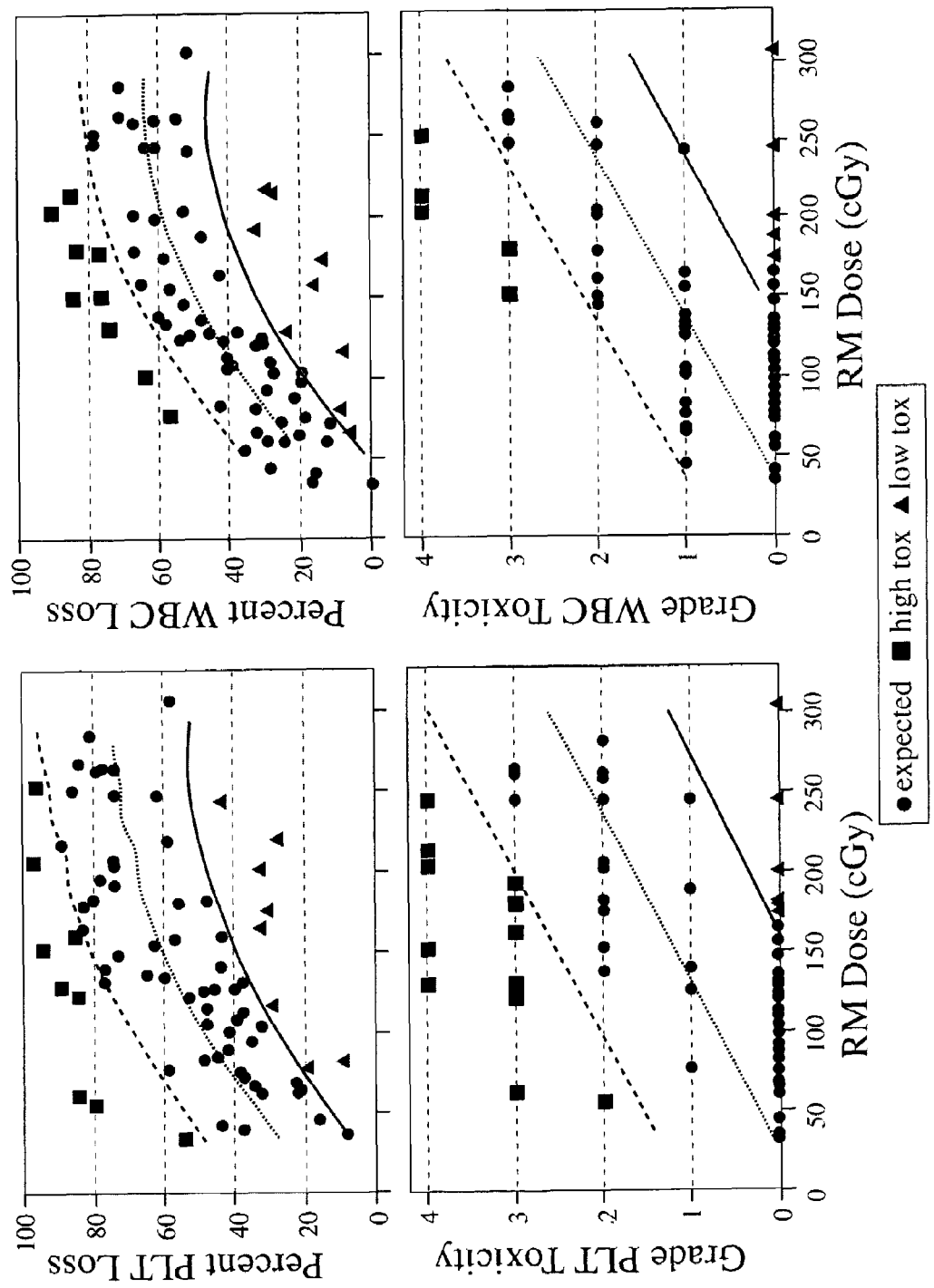
FIG. 1. Scattergram representation of 76 patients given different red marrow doses of RAIT and the (a) percent platelet (PLT) loss; (b) percent WBC loss, (c) grade PLT toxicity and (d) grade WBC toxicity shown. All patients had normal initial pWBC and PLT counts at the time of cytotoxic therapy (RAIT). {Open circles=normal toxicity; closed squares=higher than expected toxicity and open triangles=lower than expected toxicity}. Twenty-three patients were omitted because they either had BM involvement on two or more known metastases or they had higher than normal values of either pWBCs ($>10,000/mm^3$) or PLTs ($>5.times. 10^5/mm^3$).

As used herein, "myelosuppression" refers to the suppression of one or more components of hematopoiesis, which manifests in aberrant levels of one or more of the cell types that are the products of this process. For a review of hematopoiesis, and characteristics of hematopoietic cells, see CLINICAL IMMUNOLOGY: PRINCIPLES AND Practice, Vol. 1, Ch. 2, pp. 15-24 (Lewis and Harriman, eds. Mosby—Year Book, Inc. 1996), which pages are hereby incorporated by reference. On a general level it refers to decreases in white blood cell (WBC) and/or platelet counts. It also refers, on a more specific level, to suppression of one or more of the following cells that result from hematopoiesis: B-cells, T-cells, natural killer cells, dendritic cells, macrophages, neutrophils, eosinophils, basophils, mast cells and platelets. On the other hand, therefore, "myelorecovery" is the opposite of myelosuppression.

As used herein, a "stimulatory cytokine" is one that promotes hematopoiesis at one or more stages of differentiation. Stimulatory cytokines include SCF, FLT-3-L, IL-1, IL-3, IL-6, IL-11, and others known to the skilled artisan.

As used herein an "inhibitory cytokine" has a negative effect on one or more stages of hematopoiesis. Exemplary inhibitory cytokines include MIP-1α, TGFβ3, TNFα and others known in the art.

As used in a general sense herein, unless otherwise indicated by context, the term "antibody" includes "antibody fragment" and other forms of reengineered antibody subfragments which retain the ability to bind to the specific antigen to which they were developed.

B. Principles of the Invention

The invention relates to the ability to predict myelorecovery after a subject experiences myelosuppression (e.g., after radiation, cytotoxic chemotherapy, or other means) by monitoring various inhibitory and stimulatory cytokines. The present inventors have discovered that threshold levels of certain cytokines can be used to guide the health-care professional in using myelosuppressive therapies. In particular, these threshold levels provide a marker, indicating whether or not a patient will tolerate such therapy. A common application is in monitoring cytoreductive therapies, where the subject threshold levels are used to decide whether a patient is sufficiently recovered from one dose of a myelosuppressive agent to tolerate another, perhaps increased dose.

The cytokine levels monitored in the inventive methods include the so-called "early" stimulatory cytokines and the inhibitory cytokines. To be useful in these methods and kits, a statistically significant threshold level of the cytokine (or a combination of them) that correlates with myelosuppressive recovery is ascertainable. The artisan will be familiar with such statistical analysis and may readily ascertain such threshold levels, as demonstrated below in the Examples.

In a broad sense, a threshold level may be a level that is found in a normal volunteer, any deviation associated with myelosuppression being indicative of that state. In particular, the threshold level should be set such that specificity [(true negative) divided by (true negative plus total population)], accuracy [(true positive plus true negative) divided by (total population)] and sensitivity [(true positive) divided by (true positive plus false negative)] are maximized. The artisan will recognize, however that such maximization often represents a trade-off, since higher specificity, accuracy or sensitivity can result in the others being lowered. Some inventive methods yield greater than about 65% specificity, accuracy and sensitivity, while some preferred methods yield at least about 75% specificity, accuracy and sensitivity.

"Early" stimulatory factors include, but are not limited to, SCF, FLT-3-L, IL-1, IL-3, IL-6, and IL-11. These factors are thought to be involved in the early stages of myelorecovery. Thus, when they are present, the damage should be at its worst. Accordingly, a statistically significant threshold should be ascertainable, which, when exceeded, counsels against continued therapy or indicates reducing the dose.

Inhibitory cytokines, in contrast, likely are present when myelosuppressive recovery is virtually complete, when the process is turning itself off. Hence, the threshold level for these cytokines will represent a minimum level, below which therapy should be reduced or halted. Exemplary inhibitory cytokines include MIP-1α, TGFβ3 and TNFα.

The invention also contemplates the usefulness of trends in predicting myelorecovery. Thus, it is possible that the absolute amount of plasma cytokine needs to be coupled with the duration since the cytokine reached its peak. For example, as seen below in the working examples, since the values for FLT3-L ranged from below 100 pg/ml to over 400 pg/ml, it is possible that readings of FLT3-L in or just above the normal range may need to be evaluated again a few days later to determine whether plasma FLT3-L is on the rise, or is returning back down to baseline levels after being elevated. It is contemplated that those patients whose FLT3-L levels have returned to normal and maintained a normal baseline level for several weeks can tolerate higher doses than patients who have recovered only days earlier from a myelosuppressive episode and elevated FLT3-L. This provides an explanation of the low toxicity group that does not strictly correlate with any of the cytokines measured.

C. Kits of the Invention

The kits according to the invention typically comprise at least one cytokine-specific detection reagent. Some kits contain at least two cytokine-specific detection reagents. In most cases, each reagent will be adapted to detect a threshold level of cytokine, which correlates with the myelosuppressive state of a patient. In one aspect, the invention contemplates a kit for assessing the myelosuppressive state of a patient, which is useful in guiding the physician in choosing an optimal treatment regimen. They may be applied, for example, to monitor myelosuppressive treatments, to monitor efficacy of myelostimulatory treatments and to monitor recovery from myelosuppressive disorders.

Some embodiments of the present kits contain the detection reagent in association with a suitable testing substrate. Suitable substrates include "dipsticks," test-strips, microtiter plates, microscope slides, and the like. The kits of the invention generally implement the methods, described below, and should be read in that context.

Cytokine-Specific Detection Reagents

The cytokine-specific detection reagent of the kit generally confers the ability to detect specifically the cytokine of interest, in some cases quantitatively. Typically this reagent will be able to bind specifically to a cytokine, and will be detectable, directly or indirectly. For instance, the reagent may be an antibody, and may comprise a detectable label, such as a radionuclide, an enzyme or a fluorescent tag. The label may be detected, for example, using conventional immunoassays, which include enzyme-linked immunosorbant assays (ELISAs), radioimmunoassays (RIAs), and the like. Suitable methods can be found in CURRENT PROTOCOLS IN MOLECULAR BIOLOGY, Chapter 11 (Ausubel et al., eds., John Wiley & Sons, Inc. 1997), which is hereby incorporated by reference.

Due to their recognized ability to bind specifically and to their ease of production, antibodies are contemplated as a means of conferring the cytokine-binding ability of the detection reagent. Antibodies include, but are not limited to polyclonal antibodies, monoclonal antibodies (mAbs), humanized or chimeric antibodies, single chain antibodies including single chain Fv (scFv) fragments, Fab fragments, F(ab')$_2$ fragments, fragments produced by a Fab expression library, epitope-binding fragments, and multivalent forms of any of the above.

In general, techniques for preparing polyclonal and monoclonal antibodies as well as hybridomas capable of producing the desired antibody are well known in the art (Campbell, MONOCLONAL ANTIBODY TECHNOLOGY: LABORATORY TECHNIQUES IN BIOCHEMISTRY AND MOLECULAR BIOLOGY, (Elsevier Science Publishers 1984); St. Groth et al., J. Immunol. Methods 35:1-21 (1980); Kohler and Milstein, Nature 256:495-497 (1975)), the trioma technique, the human B-cell hybridoma technique (Kozbor et al., Immunology Today 4:72 (1983); Cole et al., in MONOCLONAL ANTIBODIES AND CANCER THERAPY, Alan R. Liss, Inc. (1985), pp. 77-96). Affinity of the antisera for the antigen may be determined by preparing competitive binding curves, as described, for example, by Fisher, Chap. 42 in: MANUAL OF CLINICAL IMMUNOLOGY, 2d ed., (Rose and Friedman, eds., Amer. Soc. For Microbiology 1980).

Antibody fragments include any portion of the antibody which includes the paratope and is capable of binding a cytokine of interest. Antibody fragments specifically include F(ab')$_2$, Fab, Fab' and Fv fragments. These can be generated from any class of antibody, but typically are made from IgG or IgM. They may be made by conventional recombinant DNA techniques or, using the classical method, by proteolytic digestion with papain or pepsin. See CURRENT PROTOCOLS IN IMMUNOLOGY, chapter 2, (Coligan et al., eds., John Wiley & Sons 1991-92).

F(ab')$_2$ fragments are typically about 110 kDa (IgG) or about 150 kDa (IgM) and contain two antigen-binding regions, joined at the hinge by disulfide bond(s). Virtually all, if not all, of the Fc is absent in these fragments. Fab' fragments are typically about 55 kDa (IgG) or about 75 kDa (IgM) and can be formed, for example, by reducing the disulfide bond(s) of an F(ab')$_2$ fragment. The resulting free sulfhydryl group(s) may be used to conveniently conjugate Fab' fragments to other molecules, such as localization signals.

Fab fragments are monovalent and usually are about 50 kDa (from any source). Fab fragments include the light (L) and heavy (H) chain, variable ($V_L$ and $V_H$, respectively) and constant ($C_L$ $C_H$, respectively) regions of the antigen-binding portion of the antibody. The H and L portions are linked by one or more intramolecular disulfide bridges.

Fv fragments are typically about 25 kDa (regardless of source) and contain the variable regions of both the light and heavy chains ($V_L$ and $V_H$, respectively). Usually, the $V_L$ and $V_H$ chains are held together only by non-covalent interactions and, thus, they readily dissociate. They do, however, have the advantage of small size and they retain the same binding properties of the larger Fab fragments. Accordingly, methods have been developed to crosslink the $V_L$ and $V_H$ chains, using, for example, glutaraldehyde (or other chemical crosslinkers), intermolecular disulfide bonds (by incorporation of cysteines) and peptide linkers. The resulting Fv is now a single chain (i.e., scFv).

Antibodies also include single chain antibodies and fragments (U.S. Pat. No. 4,946,778; Bird, Science 242:423426 (1988); Huston et al., Proc. Natl. Acad. Sci. USA 85:5879-5883 (1988); and Ward et al., Nature 334:544-546 (1989)). Single chain antibodies are formed by linking the heavy and light chain fragments of the Fv region via an amino acid bridge, resulting in a single chain FV (scFv).

Some exemplary kits contain at least one cytokine-specific reagent that is specific for FLT3-L, TNF-α or TGF-β. In one aspect of the invention, the reagent comprise an enzyme-linked antibody or antibody fragment.

Adapting the Reagent to Detect a Threshold

The kits of the invention detect a specific threshold of cytokine, which correlates with the myelosuppressive state of the patient. Such thresholds, and their determination, are detailed below. For convenience, it is advantageous to adapt the cytokine-specific detection reagent(s) to detect a certain threshold. In this way, a "yes" or "no" answer can be provided, generally indicating whether the patient is myelosuppressed or not. Thus, for example, colorimetric detection might be employed, whereby the presence of color indicates that a threshold level, correlating with the myelosuppressive state, has been reached.

Typically, the reagents of various assays (e.g., ELISAs, RIAs, RT-PCRs, and the like) will be able to detect levels of the target cytokine(s) that are lower than the threshold, i.e., they are more sensitive than they need to be. The artisan will be well-aware of methods of reducing the sensitivity of the present systems in order to provide a signal at a given threshold level. A particularly useful kit will include a reagent system that can provide a "yes" or "no" answer as to whether a patient has recovered sufficiently from myelosuppression to tolerate further cytotoxic therapy.

Using the Kits of the Invention

The kits may be adapted for private to commercial-scale use, for the convenience of the individual clinician, the clinical research center and even commercial diagnostic laboratories. For example, in a private clinical setting, a "dipstick"-type arrangement may be convenient. In one aspect, the cytokine-specific detection reagent may come applied to the dipstick. Thus, the kit may be used by contacting a patient sample to the dipstick-associated reagent. The detection reagent may then be visualized using conventional colorimetric means, for example. Of course, another arrangement may call for contacting the sample with the dipstick, and then application of the cytokine-specific detection reagent; the exact arrangement is a matter of choice.

In another example especially suitable for larger laboratories, the kits can be implemented in microtiter plates (e.g., 96-well plates). The same arrangement of reagents would apply, where the detection reagent is either supplied in the plate or is added after the sample is applied to the plate. In any event, given the availability of high-throughput readers for microtiter plates, very large numbers of samples could be handled automatically in this manner. Again, specific arrangements are a matter of design choice.

Methods of the Invention

The invention provides a general method of assessing the myelosuppressive state of a patient. The basic method comprises comparing the amount of at least one cytokine to a threshold level. The myelosuppressive state of the patient is then gauged relative to that threshold. The cytokines monitored, as explained above, may be early stimulatory or inhibitory cytokines, or combinations thereof. In one aspect, the method involves at least monitoring levels of FTL3-L.

When plasma samples are used in the present methods, it is advisable to assure the amounts measured are a function of marrow cell production, and not peripheral blood cell or tumor cell production. Fortunately, peripheral blood cells by themselves are unable to produce most cytokines. In fact, PCR amplification of reverse-transcribed RNA from peripheral blood cells in healthy individuals reveals that TGFβ, MIP-1α and IL-1β were expressed, but that SCF, IL-6, G-CSF, GM-CSF, IL-1α were not expressed. Cluitmans et al., Ann. Hematol. 75(1-2):27-31 (1997). Moreover, tumor-produced cytokines may confound marrow-produced cytokines. Several cytokines including TGFβ and TNFα are elevated in blood samples from ovarian, cervical, and endometrial cancer patients. Chopra et al., J. Cancer Res. Clin. Oncol. 123:167-172 (1997); Chopra et al., Cancer J. Sci. Am. 2:279-285 (1996); Chopra et al., Cancer Investigation 16(3):152-159 (1998). However, there is no indication whether this is true for all cancer types or that there is any evidence that FLT3-L, SCF, or MIP-1α are produced by tumors. The artisan will readily understand how to test and control for marrow-derived production.

The inventive methods may be used in conjunction with conventional therapies that induce myelosuppression, or where subjects have been exposed to ionizing radiation. Thus, where the threshold level is approached or crossed, therapy generally will be halted or reduced. If a patient is then re-tested, and this test indicates that the threshold is no longer approached or crossed, therapy may resume. On the other hand, where a patient is being treated, and the inventive test indicates that the threshold has not been approached or crossed, the next therapeutic dose may be administered safely. In this manner, dosing regimens may be informed by constant monitoring, increasing dose and frequency until threshold levels are approached or crossed, at which point dosing may be decreased or eliminated. In this context, a threshold level is approached when a cytokine level is within at least about 15% of the threshold number, but preferably is within at least about 10% of the threshold.

Preferred cytokines for monitoring in the present methods include FLT3-L, TNF-α and TGF-β. Since FLT3-L is an early stimulatory cytokine, the relevant threshold is a maximum. On the other hand, since TNF-α and TGF-β are inhibitory cytokines, the relevant threshold is a minimum. Exemplary threshold levels include: at least about 135 pg/ml of plasma for FTL3-L; at most about 0.5 pg/ml of plasma for TNF-α; and at most about 15 pg/ml of plasma for TGF-β. Again, it is not only these absolute thresholds that are important; the artisan will also recognize that trends toward these thresholds are significant in prediction, especially when viewed over a multi-day (1-3) temporal window.

One aspect of the invention contemplates a method of treating cancer that involves administering to a patient in need of treatment, an effective amount of an anti-cancer agent and using the present myelorecovery monitoring techniques to inform treatment, especially dosing. Thus, cytokine levels may be evaluated at intervals throughout treatment, beginning before or after the first administration of an anti-cancer agent.

Conventional anti-cancer agents include chemotherapeutics and radiation-based therapies. Chemotherapeutic agents include alkylating agents, antimetabolites, various natural products (e.g., vinca alkaloids, epipodophyllotoxins, antibiotics, and amino acid-depleting enzymes), and taxanes. Specific classes of agents include nitrogen mustards, alkyl sulfonates, nitrosoureas, triazenes, folic acid analogues, pyrimidine analogues, purine analogs, platinum complexes, adrenocortical suppressants. Some exemplary compounds include actinomycin, cyclophosphamide, chlorambucil, CPT-11, methotrexate, fluorouracil, cytarabine, thioguanine, vinblastine, vincristine, doxorubicin, daunorubicin, mitomycin, cisplatin, hydroxyurea, taxols, and platinum compounds, including oxaliplatin. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications, incorporated herein in their entirety by reference. Other suitable chemotherapeutic agents, such as experimental drugs, are known to those of skill in the art. The known dosing protocols for these drugs may be optimized using the present methods of evaluating myelosuppression.

The invention provides a method of assessing the state of the bone marrow of a patient, comprising comparing the amount of at least one hematopoietic cytokine in a sample from the patient with a threshold level, thereby gauging the state of the bone marrow of a patient. In one embodiment of the invention, the patient is in a myelosuppressive state. Preferably, the hematopoietic cytokines are FLT3-L, TNF-α and TGF-β.

In another embodiment, the present invention provides a method of assessing myelorecovery in a patient comprising repeatedly assessing the state of the bone marrow in a patient while the patient is undergoing successive treatments of myelosupressive therapy.

The invention further provides a method of predicting the bone marrow toxicity dose delivered to a subject. Preferably, the FLT3-L levels in a subject's blood or plasma are determined and the calculated bone marrow radiation dose is adjusted according to the plasma or blood level of FLT3-L in the subject. In one embodiment of the present invention, prior to measuring plasma or blood level of FLT3-L in the subject, the subject was given cytotoxic chemotherapy and/or radioimmunotherapy. In an embodiment of the present invention, such cytotoxic chemotherapy is ionizing radiation which was delivered by radioimmunotherapy.

The FLT3-L levels in a subject can be measured at least once but additional measurements of FLT3-L levels are also contemplated to predict whether the FLT3-L levels are on the rise or in the process of falling from their peak. Preferably, the FLT3-L plasma or blood levels are measured at least once before and once after potential myelosuppressive therapy.

Bone marrow radiation dose can be determined by a variety of methods. Specifically, a pretherapy tracer study performed before treatment of the subject can be used to determine the red marrow radiation dose. Preferably, the pretherapy tracer study can be performed 1-2 weeks prior to treatment. Specifically, after a subject is given a diagnostic antibody activity infusion, blood cumulated activity concentrations and total body cumulated activities can be determined. Preferably, blood cumulated activity concentrations are determined by counting samples of whole blood in a calibrated gamma well counter to obtain blood activity concentrations at various time points after the end of the antibody activity infusion. These time-activity concentration curves can be analyzed to determine the slopes of the distribution and elimination phases and their respective intercepts. Preferably, a nonlinear least squares curve-fitting algorithm is used to fit the curve. These curves can then integrated to obtain the blood cumulated activity concentration. Total body cumulated activities can also be determined. Preferably, total body cumulated activities can be determined using either whole-body gamma camera counts or handheld radiation probe counts obtained at multiple time points post-administration. Additional methods of determining blood cumulated activity concentrations and total body cumulated activities are readily apparent to one of skill in the art and are encompassed by the present invention.

Additional methods can be used to characterize the red marrow biokinetics, including determination of the red marrow cumulated activity from scintillation camera image-based analyses (Siegel J A, Lee R A, Pawlyk D A, Horowitz J A, Sharkey R M, Goldenberg D M. Sacral scintigraphy for bone marrow dosimetry in radioimmunotherapy. Nucl Med Biol. 1989; 16:553-559), compartmental modeling techniques (Loh A, Sgouros G, O'Donoghue J A, et al. Pharmacokinetic model of iodine-131-G250 antibody in renal cell carcinoma patients. J Nucl Med. 1998; 39:484-489), or use of magnetic resonance spectroscopy to provide a patient-specific estimate of the red marrow extracellular fluid fraction (Ballon D, Jakubowski A, Gabrilove J, et al. In vivo measurements of bone marrow cellularity using volume-localized proton NMR spectroscopy. Magnetic Reson Med. 1991; 19:85-95).

The invention further provides a method of determining the dose of myelosuppressive treatment delivered to the bone marrow in a subject by measuring the level of FLT3-L in the subject; using the ratio of FLT3-L in the subject to the level in normal subjects to adjust the dose of myelosuppressive treatment delivered to the bone marrow. In one embodiment of the invention, the myelosuppressive treatment is cytotoxic chemotherapy or radioimmunotherapy.

In an embodiment of the present invention, the FLT3-L level in a normal subject is from about 40 pg/mL to about 85 pg/mL, and most preferably the FLT3-L levels are about 80 pg/mL.

Bone marrow radiation dose determined by the above methods is then used to determine a treatment activity prescription.

EXAMPLES

Example 1

Methods of Use for Practicing the Invention

Patient Population and Collection of Patient Blood.

Solid tumor patients enrolled in Institutional Review Board-approved Garden State Cancer Center clinical radioimmunotherapy ("RAIT") trials have had multiple cycles of previous chemotherapy using various drugs (e.g., doxorubicin, methotrexate, topotecan, cyclohexyl-chloroethylnitrosourea (CCNU), mitomycin, etc.) and different durations ranging from 1 to 24 months since their previous treatment. Juweid et al., Cancer 80:2749-2753 (1997). Patient blood (3 ml) was collected on the day of scheduled radioimmunotherapy into citrate-tubes and complete blood counts (CBCs) were performed to establish pWBC and PLT counts. Blood was collected every 3-7 days after RAIT and the maximum percent loss, and toxicity grade for both WBCs and PLTs were determined.

Plasma Cytokine Immunoassays.

Plasma FLT3-L, SCF, and TGF-$\beta$ in patient blood samples were measured by R&D Quantikine Immunoassay kits (Minneapolis, Minn.). These assays employ a quantitative sandwich enzyme immunoassay. The optical density (OD) at 570 nm is subtracted from the OD at 450 nm to correct for plate imperfections. Average duplicate readings for each sample are read from a linear standard curve. TNF$\alpha$ and MIP-1$\alpha$ were analyzed by CYTImmune Sciences' competitive enzyme immunoassay kits (College Park, Md.), resulting in an inverse relationship between OD and concentration. The kits use an amplified color generation system in which the alkaline phosphatase reaction provides a cofactor that initiates a redo cycling reaction leading to the formation of a colored (formazan) red product. The OD was read at 492 nm. All assay kits have high sensitivity, are specific, and show no significant cross-reactivity with any other murine or human cytokine.

Red Marrow Dosimetry.

The red marrow dose was estimated in all patients from the cumulated activity in the blood based on the blood clearance data, and taking into account the contribution from the whole body activity. The use of a marrow/blood activity concentration ratio of 0.36 was used, which is consistent with the recommendations of the Dosimetry Task Group of the American Association of Physicists in Medicine. Siegel et al., Antibody Immunoconj. Radiopharm. 3:213-233 (1990); Fisher et al., Cancer 73:905-911 (1994); Sgouros et al., J. Nucl. Med. 34:689-694 (1993). The corrected blood activity concentration was always multiplied by 1,500, the weight in grams of the marrow in an average adult. The mean dose in cGy was then obtained according to the MIRD schema, taking into account the contribution from the whole body activity. Loevinger et al., Soc. Nucl. Med. (1976); Cloutier et al., J. Nucl. Med. 14:53-55 (1973).

Toxicity Assessment.

Myelotoxicity was graded according to the National Cancer Institute (NCI) toxicity criteria. All patients given therapeutic doses were followed for hematological toxicity by monitoring CBCs weekly. In case a grade 2 thrombocytopenia or leukopenia developed, biweekly measurements were taken, and in the case of grade 3 or 4 thrombocytopenia or leukopenia, measurements were taken every other day until the nadir had been determined. The patient's blood counts were followed until complete hematological recovery was established.

Statistical Analysis.

Single factor analysis of variance (F-test) was performed on serum cytokine measurements in normal volunteers, chemotherapy naive cancer patients, and cancer patients with either normal levels, lower-than-expected levels, or higher-than-expected levels of myelosuppression for their given RM dose. The ability of a single marker or a combination of serum cytokine markers to predict myelosuppressive responses was determined using the following formula: Sensitivity=[TP/(TP+FN)]; specificity=[TN/(TN+FP)]; and accuracy=[(TP+TN)/(TP+TN+FN+FP)], where TP=true positive; TN=true negative; FP=false positive; and FN=false negative.

In a true-positive, a stimulatory-cytokine is elevated and/or an inhibitory cytokine is below normal and the patient experiences high-toxicity. A true-negative means the stimulatory cytokines and/or the inhibitory cytokines are normal and toxicity is within normal limits. A false-positive means a stimulatory cytokine is elevated and/or an inhibitory cytokine level is below normal, but the magnitude of toxicity is within the expected range or low. A false-negative means stimulatory and/or inhibitory cytokines are within normal limits, but toxicity is high and could not be predicted. An alternative clinically useful measure to express test efficiency is the likelihood ratio to characterize behavior of the diagnostic test. The positive likelihood ratio (LR+) is defined as the ratio of sensitivity over (1-specificity). When it exceeds 1, the odds favoring positive diagnosis increase, and as it approaches 1, the test is indeterminate. The negative likelihood ratio (LR−) is defined as (1-sensitivity) over specificity. Simel et al., J. Clin. Epidemiol. 44:763-770 (1991).

Example 2

Ascertaining a Statistically Significant Threshold Level of a Given Cytokine

Seventy-four solid-tumor patients were selected from an initial ninety-nine patients by omitting all individuals with bone marrow metastases and all patients with an initial WBC or PLT count that was unusually high (>10,000 WBC/mm$^3$ or >550,000 PLT/mm$^3$). All patients were refractory to chemotherapy and entered clinical RAIT trials at our research center. The RM dose delivered from the therapeutic dose was calculated for each person. WBC and PLT toxicity were determined at the nadir as the percent loss from the initial count (upper panels) or as grade toxicity (lower panels), and the results plotted against the RM dose (FIG. 1). The majority of patients (52-56 out of 74 for percent loss and 40-44 out of 74 for grade toxicity) conformed to a well-defined linear relationship between RM dose and toxicity (O).

However, some patients (8 to 13) clearly exhibited less toxicity than was expected, given their RM dose (Δ) and other patients experienced much greater toxicity (9 to 15) than most other patients did (●). Using percent loss, only 5 individuals who did not fit the linear pattern deviated for both WBCs and PLTs, 2 with excess toxicity for both and 3 with less-than-expected toxicity for both. Thirteen had excess PLT toxicity with normal WBC toxicity and 5 had excess WBC toxicity and normal PLT toxicity. Using grade of toxicity as a criterion, 7 individuals deviated from expectations; 2 with excess WBC and PLT toxicity and 5 with less toxicity for both than was expected. An additional 8 patients had excess PLT toxicity with normal WBC toxicity and 7 had excess WBC toxicity, but normal PLT toxicity (Table 1A).

Since an excess toxicity of either WBC or PLT becomes dose-limiting, all patients who deviated even in one category would benefit from availability of a marker to predict excess-toxicity. Of those individuals with excess PLT toxicity (15 with excess % loss and 10 with excess grade), 9 were elevated for both, only 1 has excess grade but a normal % loss and 5 had an excess % loss, but a normal grade toxicity. Of those individuals with excess WBC toxicity (9 with excess % loss and 11 with excess grade toxicity), 5 were high for both parameters measured, and 6 were high for grade toxicity but had a normal % loss, and 3 had a high % loss but a normal grade toxicity (Table 1B). If patients demonstrate a high initial WBC and/or PLT count on the day of RAIT (upper end of normal range), they could conceivably experience a high percent loss but a reasonable grade toxicity. If WBC and/or PLT counts start out at the low end of the normal range on the day of RAIT, then the patient may experience a high grade toxicity but not a high percent loss.

TABLE 1

Summary of the Number of Patients with Abnormal Degree of Toxicity in Response to RAIT (based on scattergram in FIG. 1)

A. Effect on WBCs and/or PLTs

| Measurement: | Both WBCs and PLTs Effected | | WBCs only Effected | | PLTs only Effected | |
| --- | --- | --- | --- | --- | --- | --- |
| | High | Low | High | Low | High | Low |
| Percent Loss | 2 | 3 | 5 | 6 | 13 | 5 |
| Grade Toxicity | 2 | 5 | 9 | 6 | 8 | 8 |

Note:
Total of 74 patients included in the analysis.

B. Percent Loss and Grade Toxicity

| | N | Excess % Loss | Excess Grade | Excess-Both | Excess Grade-Normal % Loss | Excess % Loss - Normal Grade |
| --- | --- | --- | --- | --- | --- | --- |
| Excess PLT Toxicity | 16 | 15 | 10 | 9 | 1 | 6 |
| Excess WBC Toxicity | 15 | 11 | 9 | 5 | 6 | 4 |

Note:
All patients has multiple cycles of chemotherapy between 1 and 24 mo. prior to entering these RAIT clinical trials.

From the patients described, thirty-nine individuals were selected and sorted them into three subgroups, the first showing "normal" WBC and PLT toxicity (N=14), the second showing low toxicity (N=13), and the third demonstrating "high" WBC or PLT toxicity (N=12). As shown in Table 2, the three groups received similar RM doses (139±28 vs. 190±32 vs. 141±51 cGy, respectively). All three groups had similar initial WBC (6,000±2,000/mm$^3$ in the first group vs. 8,000±2,000/mm$^3$ in the latter two groups) and initial PLT counts (280,000±112,000/mm$^3$ vs. 233,000±84,000/mm$^3$ vs. 203,000±65,000/mm$^3$, respectively). The group referred to as excess toxicity had a significantly higher PLT loss (81±11% vs. 54±20% in the normal toxicity group; p<0.001) and Grade PLT toxicity (3±1 vs. 1±1; p<0.001). The group also had a higher grade WBC toxicity (2±1 vs. 1±1; p<0.05).

was not significantly different, however, from other groups because of a marked variability between patients (2.62±1.03 compared with normal toxicity patients 1.50±0.33 pg/ml or 1.80±0.54 pg/ml in the untreated volunteers). Plasma TGFβ was also not significantly different (28.1±4.9 pg/ml in the excess toxicity group and 38.1±7.5 in the normal toxicity group). Plasma MIP1α was significantly lower in the excess toxicity group (2.23±1.09 pg/ml vs. 5.08±0.91 pg/ml in the normal toxicity group and 5.10±1.80 in the untreated volunteers group; p<0.05). However, the low toxicity group also had reduced plasma MIP1α (2.47±0.68 pg/ml; p<0.05).

Of the five plasma cytokines evaluated, FLT3-L was found to be most informative regarding anticipated toxicity as a function of RM dose. Moreover, If patient data are sorted according to toxicity grade (<grade 3, or ≧grade 3) indepen-

TABLE 2

Patient Group Characteristics for Cytokine Marker Studies.

| Variable | Normal Toxicity (N = 14) | Low Toxicity (N = 13) | Excess Toxicity (N = 12) |
| --- | --- | --- | --- |
| Months Post Chemotherapy | 4 ± 6 (range: 2 to 18) | 7 ± 9 (range: 2 to 24) | 5 ± 4 (range: 1 to 13) |
| RM Dose (cGy) | 139 ± 28 | 190 ± 32 | 141 ± 51 |
| Initial pWBC Count/μl (×1000) | 6 ± 2 | 8 ± 2 | 8 ± 2 |
| Initial PLT Count/μl (×1000) | 260 ± 112 | 233 ± 84 | 203 ± 65 |
| % pWBC Loss Post RAIT | 45 ± 21 | 42 ± 18 | 52 ± 25 (p < 0.1 = NS) * |
| % PLT Loss Post RAIT | 54 ± 20 | 43 ± 14 (p < 0.06) | 81 ± 11 (p < 0.001) |
| Grade pWBC Toxicity Post RAIT | 1 ± 1 | 0 ± 1 (p < 0.06) | 2 ± 1 (p < 0.05) |
| Grade PLT Toxicity Post RAIT | 1 ± 1 | 0 ± 0 (p < 0.01) | 3 ± 1 (p < 0.001) |

* p values are relative to normal toxicity group

Figure 2:
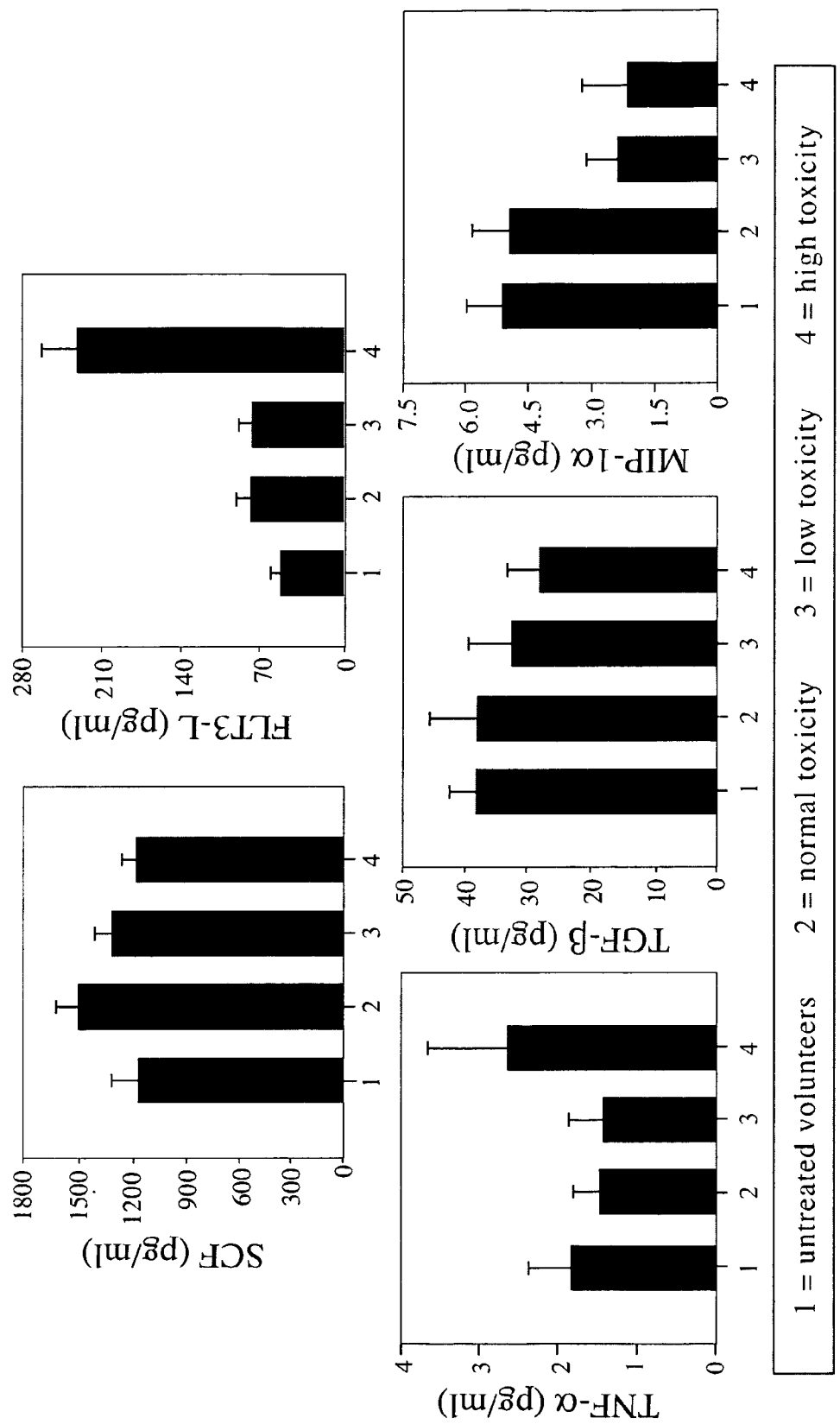
FIG. 2. Plasma cytokine levels for SCF, FLT3-L, TNFα, TGFβ and MIP-1α (mean±SEM) for 5 untreated volunteers, for 14 patients derived from the normal degree of toxicity group (open circles from FIG. 1), for 13 patients with lower than expected toxicity (triangles in FIG. 1) and 12 patients with higher than expected toxicity (solid squares in FIG. 1).
Figure 3:
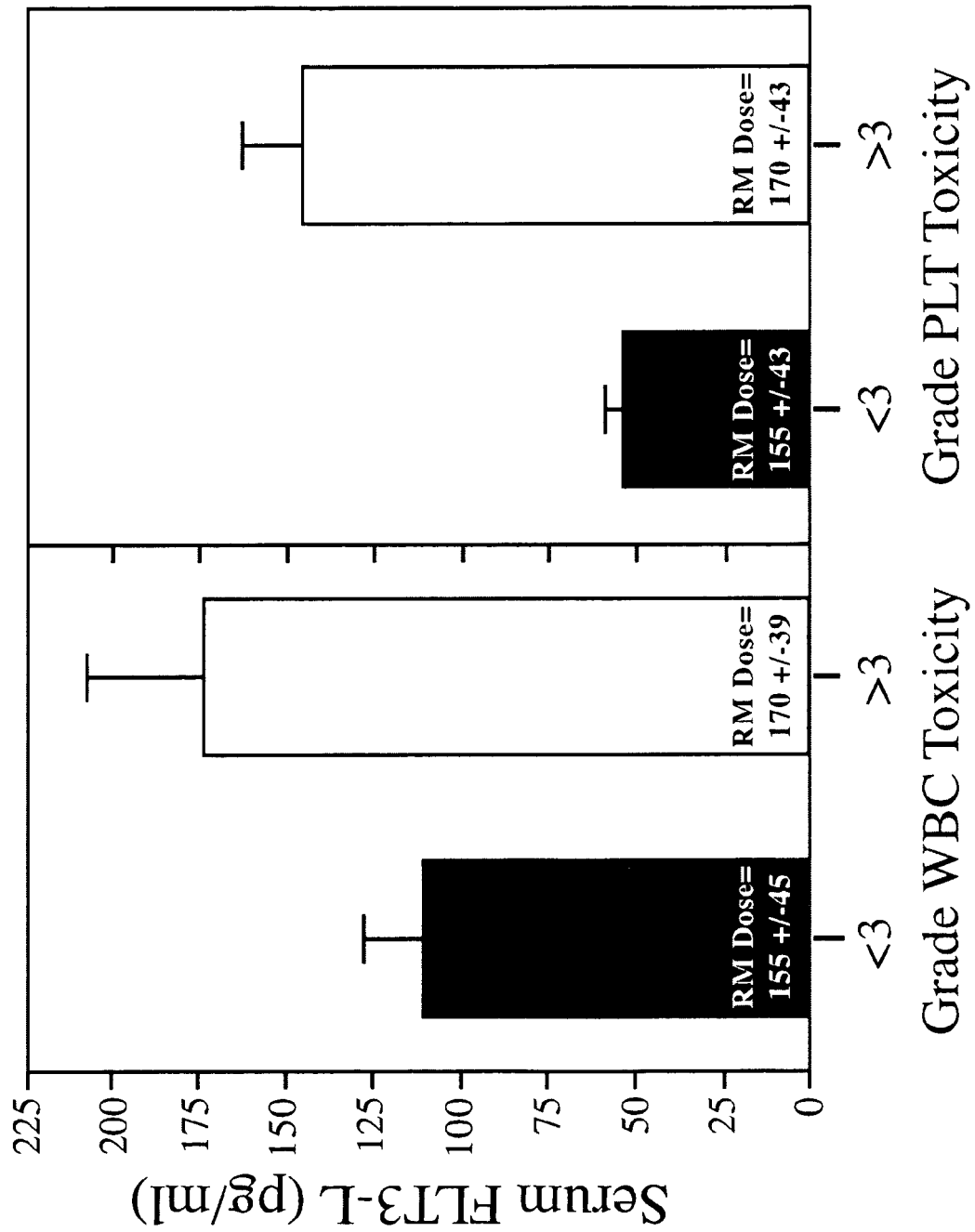
FIG. 3. Plasma FLT3-L levels (mean±SEM) for patients sorted by grade toxicity—those <grade 3 (27-28 patients) and those >grade 3 toxicity (11-12 patients). Average RM dose for all groups is noted in the base of the vertical bars and significance (t-test) noted at the top of the bar.

We tested five cytokines in patient plasma (FIG. 2) for statistical correlation to myelorecovery. Table 3 shows the cytokines tested and the characteristics of the assays used.

dent of RM dose, instead of sorting patient data by normal-, low-, or high-toxicity, the importance of FLT3-L becomes even stronger (FIG. 3). Of thirty-nine patients, 27 had <grade

TABLE 3

Characteristics of Cytokine Immunoassays

| | FLT3-L | SCF | TGFβ1 | TNFα | MIP-1α |
| --- | --- | --- | --- | --- | --- |
| Sensitivity | 7 pg/ml | 9 pg/ml | 7 pg/ml | 0.2 ng/ml | 0.2 ng/ml |
| Linearity (range %) | 105% | 104% | 013% | — | — |
| Range | 0-1000 pg/ml | 0 to 2000 pg/ml | 0 to 2000 pg/ml | 0.2 to 50 ng/ml | .2 to 50 ng/ml |
| Recovery | 94-110% | 84-112% | 94-110% | — | 85-104% |
| Normal Values | 58.6 to 130.9 | 1000 to 1790 | 15.6 to 32.4 | 1.0 to 5.0 | 15 to 46 |
| Cross-reactivity | — | — | TGF-β5-1.5% TGF-β3-0.9% | — | — |

SCF was similar in all groups studied; 1498±136 pg/ml vs. 1311±119 pg/ml vs. 1177±102 pg/ml for the normal, low, and high toxicity groups compared with 1138±183 pg/ml in untreated volunteers and 1060±217 pg/ml for cancer patients who received no prior chemotherapy. In contrast to results with SCF, the other stimulatory cytokine, FLT3-L, showed a significant elevation in the excess-toxicity group (235±29 pg/ml; p<0.001) compared with patients with normal or low toxicity (81±11 pg/ml and 79±12 pg/ml, respectively), or with untreated volunteers (52±6 pg/ml).

Surprisingly, while a reduction in inhibitory cytokines was postulated to exist in the excess toxicity group, instead plasma TNFα was higher in the excess toxicity group. This 3 PLT toxicity and 12 had ≧grade 3 PLT toxicity (the numbers are 28 and 11 patients for WBC toxicity, respectively). The RM doses for these groups were similar. Plasma FLT3-L (mean±SEM) for PLT toxicity <grade 3 was 84.4±8.8 pg/ml and 220.6±35.7 pg/ml for PLT toxicity ≧grade 3 (p<0.001). A similar tendency existed for WBC toxicity, but was not statistically significant.

The usefulness of FLT3-L alone or in combination with other plasma cytokine measurements to predict high-toxicity is presented in Table 4. Stimulatory cytokine levels were set above the upper normal limit and inhibitory cytokine levels were set below the lower normal limit, both specified in Table 3. Results are expressed as sensitivity, specificity, and accuracy; the latter measurement permits identification of both the true positives and true negatives from the total population. Of all 7 permutations evaluated, high FLT3-L levels alone (>135 pg/ml) resulted in the best values for sensitivity =0.83 (one-sided 95% confidence interval is 0.66-1). Likewise, the accuracy is 0.85 and the specificity is estimated at 0.89 (95% confidence interval being 0.79-1). Combining elevated FLT3-L levels with low TNFα or low MIP1α resulted in maximum specificity, but dramatically reduced both sensitivity (0.10 or 0.56, respectively) and accuracy (0.29 and 0.25, respectively). Alternatively, adjusting the threshold for FLT-3 to 170 pg/ml results in a reduced sensitivity of 0.62, but an increased specificity of 1.0 and no significant change in accuracy (0.87) compared with a FLT3-L cutoff of 135 pg/ml. Thus, the threshold set for FLT3-L will determine whether sensitivity or specificity is higher. By using the lower FLT3-L threshold of 135 pg/ml, the positive and negative likelihood ratios can be calculated as a means of expressing predictability of FLT3-L as a diagnostic test. The estimated positive likelihood ratio is 7.5 with a 95% confidence interval 2.5-22.5. The negative likelihood ratio is 0.19, with a 95% confidence interval of 0.05-0.67.

TABLE 4

Ability of Serum Cytokines to Predict Thrombocytopenia *

|  | Sensitivity | Specificity | Accuracy |
| --- | --- | --- | --- |
| High FLT3-L (>135 pg/ml) | 83% | 89% | 85% |
| High FLT3-L or Low TNFα (<0.5 pg/ml) | 69% | 84% | 78% |
| High FLT3-L or Low TGFβ (<15 pg/ml) | 69% | 85% | 77% |
| High FLT3-L or Low TNFα or Low TGFβ | 50% | 83% | 75% |
| High FLT3-L and Low TNFα | 10% | 100% | 29% |
| High FLT3-L or Low MIP-1α (<10 pg/ml) | 63% | 81% | 34% |
| High FLT3-L and Low MIP1α | 56% | 100% | 25% |

* N = 39; 12 with high toxicity; 13 with low toxicity; 14 with normal toxicity for the given RM dose.

Hematopoiesis proceeds under the influence of early and late stimulatory and inhibitory cytokines (Cannistra et al., Semin. Hematol. 25:173-188 (1988); Whetton et al., Biochem. Biophys. Acta. 989:111-132 (1994)). The present data now show that measuring changes in production of one or more of these growth factors may predict when recovery has occurred after previous cytotoxic therapy.

In sum, these data show that plasma FLT3-L levels predicted excess platelet toxicity in 10 out of 12 patients (mean=225±106 pg/ml) and gave a false-positive in only 3 out of 27 other patients (mean of 80±41 pg/ml). Plasma FLT3-L>135 pg/ml resulted in an 83% sensitivity and an 85% and 89% specificity and accuracy, respectively, at predicting excess toxicity from additional cytotoxic therapy. The positive likelihood ratio is 7.5 (95% confidence interval of 2.5-22.5) and the negative likelihood ratio is 0.19 (95% confidence interval of 0.05-0.67).

Accordingly, elevated plasma FLT3-L in patients who received previous chemotherapy is a predictive measure of the stage of recovery of the marrow compartment. FLT3-L seems to identify the likelihood that the patient will experience ≧grade 3 thrombocytopenia if additional cytotoxic therapy is administered. Knowledge of marrow activity should permit therapy that is more aggressive by establishing the earliest possible time for dosing with any cytotoxic agent having myelosuppression as the dose-limiting toxicity.

Example 3

Adjustment of Red Marrow Dose by FLT3-L Ratio

Red marrow radiation doses were determined for 30 patients (20 males and 10 females, all without bone marrow or bone involvement, 18 had prior chemotherapy) after receiving $^{131}$I-RAIT (activity range 2.1-8.9 GBq). Radiation dose estimates were calculated using two different methods of red marrow cumulated activity and red marrow-to-blood activity concentration ratio determinations for two dosimetric models, using both male and female and male-only masses and S values. Highest platelet toxicity grade at nadir (PTG), percent platelet count decrease (PPD), and platelet nadir counts (PN) were measured. FLT3-L levels (pg/ml) were determined by immunoassay prior to treatment; a normal FLT3-L level was assumed to be 80 pg/ml. The red marrow radiation doses (cGy) were adjusted for the patient's FLT3-L level when the patient's cytokine level exceeded the normal value. Marrow doses and FLT3-L adjusted marrow doses were correlated to PTG, PPD, PN, and 1/PN. Administered activity, administered activity per unit body weight, and total body radiation dose were also correlated to these hematologic toxicity measures.

All the red marrow dose calculation schemes resulted in essentially the same correlations with the hematologic toxicity measures. Poor correlations were observed between administered activity, administered activity per unit body weight, total-body radiation dose, or red marrow radiation dose and PTG, PPD, PN and 1/PN. All correlations improved greatly when the various predictors of toxicity were adjusted for the patient's FLT3-L level. The highest correlation observed was between red marrow dose or total body dose and 1/PN (r=0.86). Using an unadjusted red marrow dose to predict toxicity ≧Grade 3, there were 8 true positive, but 13 false positive cases with 9 true negatives. However, using a FLT3-L-adjusted red marrow dose, there were 8 true positives, but only 2 false positives and 20 true negatives.

FLT3-L adjusted red marrow radiation doses provide improved correlation with hematologic toxicity. Thus, elevated FLT3-L plasma levels prior to RAIT indicate increased radiosensitivity of the bone marrow and provide better prediction of toxicity than red marrow radiation dose alone, leading to better treatment planning and minimization of toxicity by adjustment of administered activity.

MATERIALS AND METHODS

Patients and Antibodies

Thirty patients (20 male and 10 female) enrolled in institutional review board-approved Garden State Cancer Center clinical radioimmunotherapy (RAIT) trials were included in this study. No patient had known bone marrow or bone metastases. The patients received RAIT with $^{131}$I labeled anti-carcinoembryonic antigen (CEA) NP4 (IgG or F(ab')$_2$) or anti-CEA MN-14 (IgG or F(ab)$_2$, supplied by Immunomedics, Inc., Morris Plains, N.J.) (Juweid M E, Zhang C, Blumenthal R D, Hajjar G, Sharkey R M, Goldenberg D M). Prediction of hematologic toxicity after radioimmunotherapy with $^{131}$I-labeled anticarcinoembryonic antigen monoclonal antibodies. J Nucl Med. 1999; 40:1609-1616) with administered activities ranging from 2.1-8.9 GBq for the treatment of CEA-producing cancers. The treatment activity prescription was either a fixed activity of 2.8 GBq, an activity based on the patient's body surface area, or an activity determined by a pretherapy tracer study performed 1-2 wk before treatment to deliver a prescribed red marrow radiation dose. All infusions were given intravenously over a 15-30 min time period, and all patients were premedicated with Lugol's or supersaturated potassium iodine solution and potassium perchlorate to decrease thyroid and gastric uptake of radioiodine. These labeled monoclonal antibodies are known to not bind to cross-reactive antigens, especially in the red marrow (Sharkey R M, Goldenberg D M, Goldenberg H, et al. Murine monoclonal antibodies against carcinoembryonic antigen: immunological, pharmacokinetic and targeting properties in humans. Cancer Res. 1990; 50:2823-2831, Hansen H J, Goldenberg D M, Newman E, Grebenau R, Sharkey R M. Characterization of second generation monoclonal antibodies against carcinoembryonic antigen. Cancer. 1993; 71:3478-3485, Sharkey R M, Goldenberg D M, Murthy S, et al. Clinical evaluation of tumor targeting with a high affinity anticarcinoembryonic-antigen-specific, murine monoclonal antibody, MN-14. Cancer. 1993; 71:2081-2096). Twelve patients were chemotherapy-naive and the remainder had multiple cycles of previous chemotherapy using various drugs and different duration ranging from 1 to 24 months since their previous treatment.

Blood and Total-Body Pharmacokinetics

Blood-cumulated activity concentrations were determined by counting samples of whole blood in a calibrated gamma well counter to obtain blood activity concentrations at various time points after the end of the antibody activity infusion. Three to eight blood samples were collected over the first 24 h, and then daily sampling was performed over the next 2-7 d. These time-activity concentration curves were analyzed using a nonlinear least squares curve fitting algorithm to determine the slopes of the distribution ($\alpha$) and elimination ($\beta$) phases and their respective intercepts (A and B). These curves, which were either monophasic or biphasic, were then integrated to obtain the blood cumulated activity concentration. Total body cumulated activities were determined using either whole-body gamma camera counts or hand-held radiation probe counts obtained at multiple time points post-administration.

Plasma Cytokine Immunoassays

Blood samples were collected in all patients on the day of RAIT. In addition, blood samples were collected from five normal volunteers. Plasma FLT3-L in these blood samples was measured by a quantitative sandwich enzyme immunoassay using R&D Quantikine Immunoassay kits (Minneapolis, Minn.). Samples were run in duplicate and results were read from a linear standard curve. The assay kits were sensitive (7 pg/ml), specific, and showed no significant cross-reactivity with any other murine or human cytokine. The purpose of the volunteer sampling was to determine a normal FLT3-L level.

Toxicity Assessment

Myelotoxicity was graded according to the Radiation Therapy Oncology Group (RTOG) criteria. All patients given therapeutic administrations of $^{131}$I monoclonal antibodies were followed for hematologic toxicity by monitoring complete peripheral blood cell counts weekly. Patient blood was collected prior to RAIT to establish the baseline peripheral white blood cell (WBC) and platelet (PLT) counts. When Grade 2 or higher thrombocytopenia or leukopenia developed, measurements were taken more frequently until the nadir had been determined. The patients' blood counts were followed until complete hematologic recovery was established. Since thrombocytopenia is often the dose-limiting factor for RAIT, platelet toxicity grade (PTG), percent platelet decrease (PPD), and platelet nadir (PN) were used as the measures of toxicity in this study. In addition, 1/PN was determined.

Red Marrow Dosimetry

Red marrow radiation dose was estimated in all patients based on the measured cumulated activity in the whole blood and the measured cumulated activity in the total body. The relative contribution of each of these two components to the red marrow dose estimate is dependent upon the total body-to-blood cumulated activity ratio (Siegel J A, Stabin M G, and Sparks R B. Total body and red marrow dose estimates. J Nucl Med. 2003; 44:320-321). Additional distinguishable source organ contributions could also be included (Siegel J A, Wessels B W, Watson E E, et al. Bone marrow dosimetry and toxicity for radioimmunotherapy. Antibody Immunoconj Radiopharm. 1990; 3:213-233); however, their expected contribution to red marrow dose has been estimated to be on the order of 5% or less. A two-component equation (Bigler R E, Zanzonico P B, Leonard R, et al. Bone marrow dosimetry for monoclonal antibody therapy. In: Schlafke-Stelson A T, Watson E E, eds. Fourth International Radiopharmaceutical Dosimetry Symposium. Oak Ridge: Oak Ridge Associated Universities; 1986: 535-544) was therefore used to determine red marrow absorbed dose, since these patients do not have disease in bone marrow or bone and the radioimmunotherapeutic agents they received do not bind to any blood, marrow, or bone elements. The first component reflects the red marrow dose contribution associated with the activity distributed within the extracellular fluid space of the red marrow due to the circulating blood activity, and the second component reflects the absorbed dose contribution associated with the activity in the remainder of the body, according to:

$$D_{RM} = \tilde{A}_{RM} S(RM \leftarrow RM) + \tilde{A}_{RB} \times S(RM \leftarrow RB) \qquad \text{Eq. 1}$$

where $D_{RM}$ is the red marrow dose estimate, $\tilde{A}_{RM}$ is the red marrow cumulated activity, $\tilde{A}_{RB}$ is the remainder of the body cumulated activity obtained by subtracting the red marrow value, $\tilde{A}_{RM}$, from the total body value, $\tilde{A}_{TB}$, $S(RM \leftarrow RM)$ is the red marrow-to-red marrow S value, and $S(RM \leftarrow RB)$ is the remainder of the body-to-red marrow S value. Most investigators have used one of two dosimetric models, namely MIRD 11 or MIRDOSE 3 (Stabin MG. MIRDOSE: personal computer software for use in internal dose assessment in nuclear medicine. J Nucl Med. 1996; 37:538-546), for the needed S values in Equation 1. Therefore, both sets of S values and their associated masses were used to compare the red marrow dose results. Further, MIRDOSE 3 explicitly provides S values for females; therefore, an additional red marrow dose comparison was performed using both male and female versus male-only masses and S values. The model masses were always adjusted for patient weight through multiplication by the total body mass of the patient divided by the total body mass of the model; all S values were adjusted using the inverse of this mass relationship (linear mass-based scaling of the S values for $^{131}$I is not strictly correct since the photon absorbed fractions do not scale linearly with weight; however, this approximation gives adequate results). The red marrow mass of the adult male model is 1.5 kg and 1.12 kg for MIRD 11 and MIRDOSE 3, respectively, and the total-body mass of the adult male model is 69.88 kg and 73.7 kg for MIRD 11 and MIRDOSE 3, respectively. For females, the MIRDOSE 3 red marrow model mass is 1.05 kg and the model total-body mass is 58 kg. It should be noted that the remainder of the body-to-red marrow S value was determined not only by using the patient-specific approach of adjusting the model S values and masses by the patient total body weight, but also, since there is no bone activity uptake in the patients studied, the bone component (i.e., trabecular and cortical) contribution to this term was explicitly subtracted (Stabin M G, Siegel J A, Sparks R B, Eckerman K F, Breitz H B. Contribution to red marrow absorbed dose from total body activity: a correction to the MIRD method. J Nucl Med. 2001; 42:492-498).

The red marrow cumulated activity, $\tilde{A}_{RM}$, in Equation 1 was determined using two approaches:

$$\tilde{A}_{RM} = [\tilde{A}]_{blood} m_{RM,model} \frac{m_{TB,patient}}{m_{TB,model}} CF \qquad \text{Eq. 2}$$

$$\tilde{A}_{RM} = 1.443 \, T_{e,blood} \frac{m_{RM}}{m_{blood}} CF \qquad \text{Eq. 3}$$

where $[\tilde{A}]_{blood}$ is the blood cumulated activity concentration obtained from analysis of the blood activity concentration-time curve, $m_{RM,model}$ is the red marrow mass of the respective dosimetric model, $m_{TB,patient}$ is the total body mass of the patient, $m_{TB,model}$ is the total body mass of the respective model, $T_{e,blood}$ is the blood effective half-time obtained from analysis of the blood activity concentration-time curve (if the blood activity concentration-time curve was biphasic, $T_{e,blood}$ is replaced by $\Sigma_i f_i (T_i)_{e,blood}$, where $f_i$ is the activity concentration fraction of the i-th exponential component and $(T_i)_{e,blood}$ is the effective half-time of the i-th exponential component). Since the red marrow and blood masses are assumed to vary similarly as a function of patient weight, the value of the mass ratio in Equation 3 is assumed to be a fixed value. Finally, CF is a correction factor for the marrow-to-blood activity concentration ratio. Originally, the correction factor, CF, was set at unity (1), but other investigators have shown this value to be too conservative. CF is currently assigned either a fixed value of between 0.2-0.4 or a value of 0.19/(1-hematocrit) (Sgouros G. Bone marrow dosimetry for radioimmunotherapy: theoretical considerations. J Nucl Med. 1993; 34:689-694, Siegel J A, Lee R A, Pawlyk D A, Horowitz J A, Sharkey R M, Goldenberg D M. Sacral scintigraphy for bone marrow dosimetry in radioimmunotherapy. Nucl Med Biol. 1989; 16:553-559, Siegel J A, Pawlyk D A, Lee R A, et al. Tumor, red marrow, and organ dosimetry for $^{131}$I-labeled anti-carcinoembryonic antigen monoclonal antibody. Cancer Res. 1990; 50 (suppl):1039s-1042s, Siegel J A, Lee R A, Horowitz J A, et al. Bone marrow dosimetry: marrow-to-blood activity concentration ratio [abstract]. J Nucl Med. 1990; 31:788). For this analysis, two approaches have been used for red marrow radiation dose comparison: a fixed CF of 0.3 and a CF determined using the value of 0.19/(1-hematocrit).

All red marrow radiation doses (cGy) were adjusted for the patient's FLT3-L level when the patient's cytokine levels exceeded normal values. Marrow doses and FLT3-L adjusted marrow doses were correlated to PTG, PPD, PN and 1/PN. In addition, administered activity, administered activity per unit body weight, and total body dose (equal to $\tilde{A}_{TB}$ multiplied by the mass-adjusted total body-to-total body S value) were also correlated to these measures of hematologic toxicity.

RESULTS

The FLT3-L level was determined in the volunteers to be 52±14 pg/ml; therefore a normal value of FLT3-L was assumed to be 80 pg/ml (mean±2SD). The red marrow radiation doses (cGy) were adjusted for the patient's FLT3-L level (FLT3-L level/80) when the patient's cytokine level exceeded 80 pg/ml. All the red marrow dose calculation schemes resulted in essentially the same correlations with the various measures of hematologic toxicity (Table 5):

Use of MIRD 11 and MIRDOSE 3 S values and masses yielded similar correlations.

Use of male-only parameters resulted in similar correlations to use of both male and female model parameters.

Use of the two methods for red marrow cumulated activity determination (Equations 2 and 3) resulted in similar-dose-toxicity correlations.

Use of constant red marrow-to-blood activity concentration ratio (CF=0.3) yielded similar results to use of the more patient-specific CF determination.

Use of 1/platelet nadir yielded better correlations than use of platelet grade, percent decrease in platelets, or platelet nadir.

TABLE 5

Correlation Coefficients

Correlation coefficients (r)

| | Red Marrow Dose (cGy) | | Total Body | Activity | Activity/Body |
| --- | --- | --- | --- | --- | --- |
| | CF = 0.3 | CF = 0.19/(1-hct) | Dose (cGy) | (GBq) | Weight (GBq/kg) |
| 1. MIRDOSE 3 | | | | | |
| A. All Males | | | | | |
| i. Equation 3 | | | | | |
| PTG | 0.28 (0.70) | 0.25 (0.70) | 0.23 (0.68) | 0.05 (0.61) | 0.28 (0.72) |
| PPD | 0.15 (0.48) | 0.10 (0.47) | 0.06 (0.46) | 0.15 (0.51) | 0.33 (0.59) |
| PN | 0.22 (0.76) | 0.20 (0.76) | 0.16 (0.75) | 0.03 (0.60) | 0.18 (0.75) |
| 1/PN | 0.20 (0.86) | 0.19 (0.85) | 0.17 (0.86) | 0.21 (0.53) | 0.04 (0.79) |
| ii. Equation 2 | | | | | |
| PTG | 0.31 (0.68) | 0.28 (0.68) | | | |
| PPD | 0.15 (0.46) | 0.12 (0.46) | | | |
| PN | 0.27 (0.75) | 0.24 (0.74) | | | |
| 1/PN | 0.21 (0.84) | 0.17 (0.82) | | | |
| B. Males & Females | | | | | |
| Equation 3 | | | | | |
| PTG | 0.31 (0.68) | 0.27 (0.68) | | | |
| PPD | 0.15 (0.46) | 0.11 (0.45) | | | |

TABLE 5-continued

Correlation Coefficients

| | Correlation coefficients (r) | | | | |
|---|---|---|---|---|---|
| | Red Marrow Dose (cGy) | | Total Body Dose (cGy) | Activity (GBq) | Activity/Body Weight (GBq/kg) |
| | CF = 0.3 | CF = 0.19/(1-hct) | | | |
| PN | 0.27 (0.74) | 0.24 (0.74) | | | |
| 1/PN | 0.20 (0.86) | 0.18 (0.85) | | | |
| 2. MIRD 11 Equation 3 | | | | | |
| PTG | 0.31 (0.67) | 0.26 (0.67) | | | |
| PPD | 0.17 (0.46) | 0.12 (0.46) | | | |
| PN | 0.28 (0.73) | 0.23 (0.71) | | | |
| 1/PN | 0.20 (0.85) | 0.16 (0.82) | | | |

All predictors of toxicity (administered activity, administered activity per unit body weight, total body dose, and red marrow dose) when adjusted for the patient's observed FLT3-L level yielded stronger correlations than when non-adjusted.

Adjusted red marrow and total-body dose yielded better correlations than adjusted administered activity (GBq) or adjusted administered activity per unit body weight (GBq/kg) when using 1/PN as the measure of hematologic toxicity.

Figure 4:
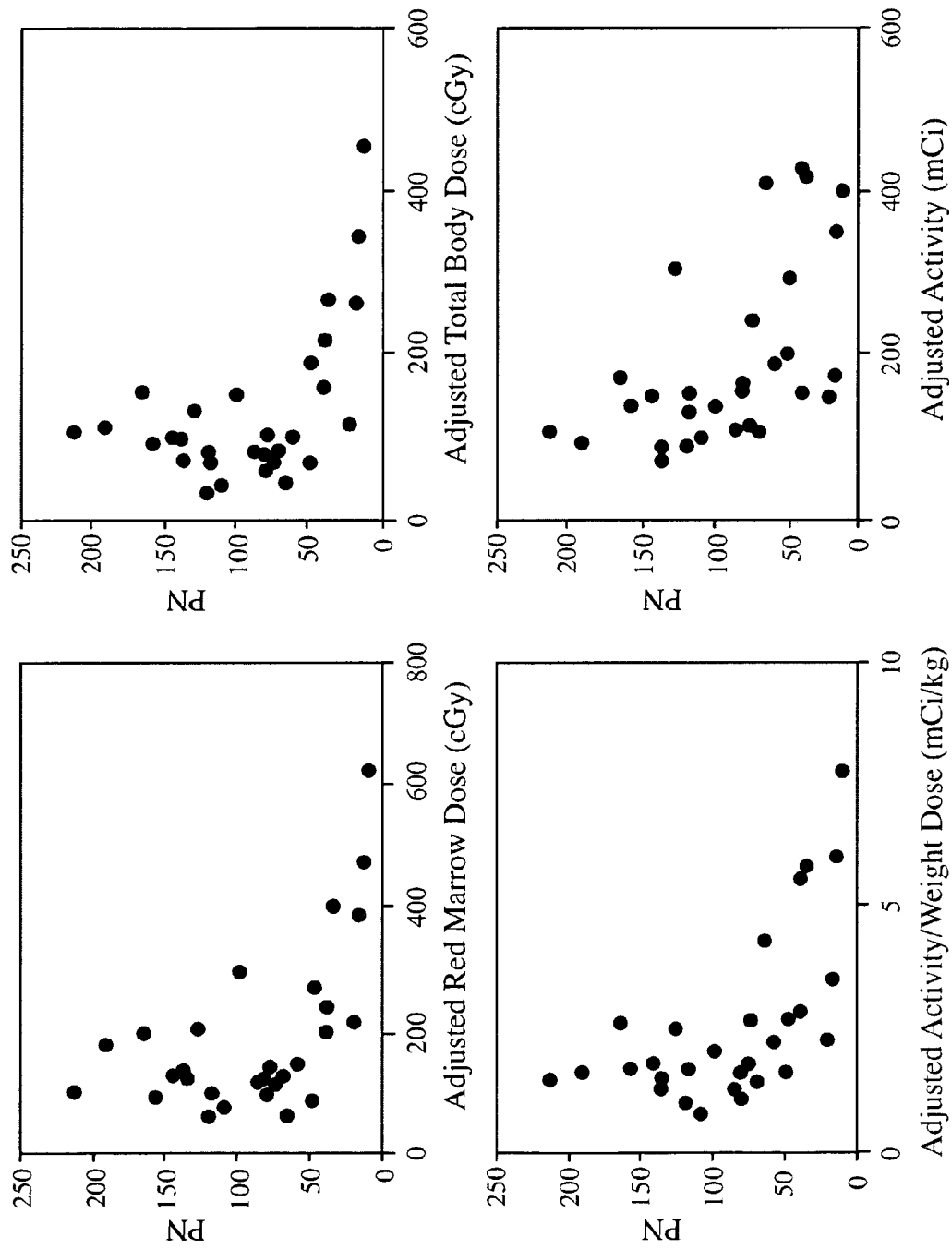
FIG. 4. Comparisons of platelet nadir (PN) with FLT3-L adjusted predictors of toxicity.
Figure 5:
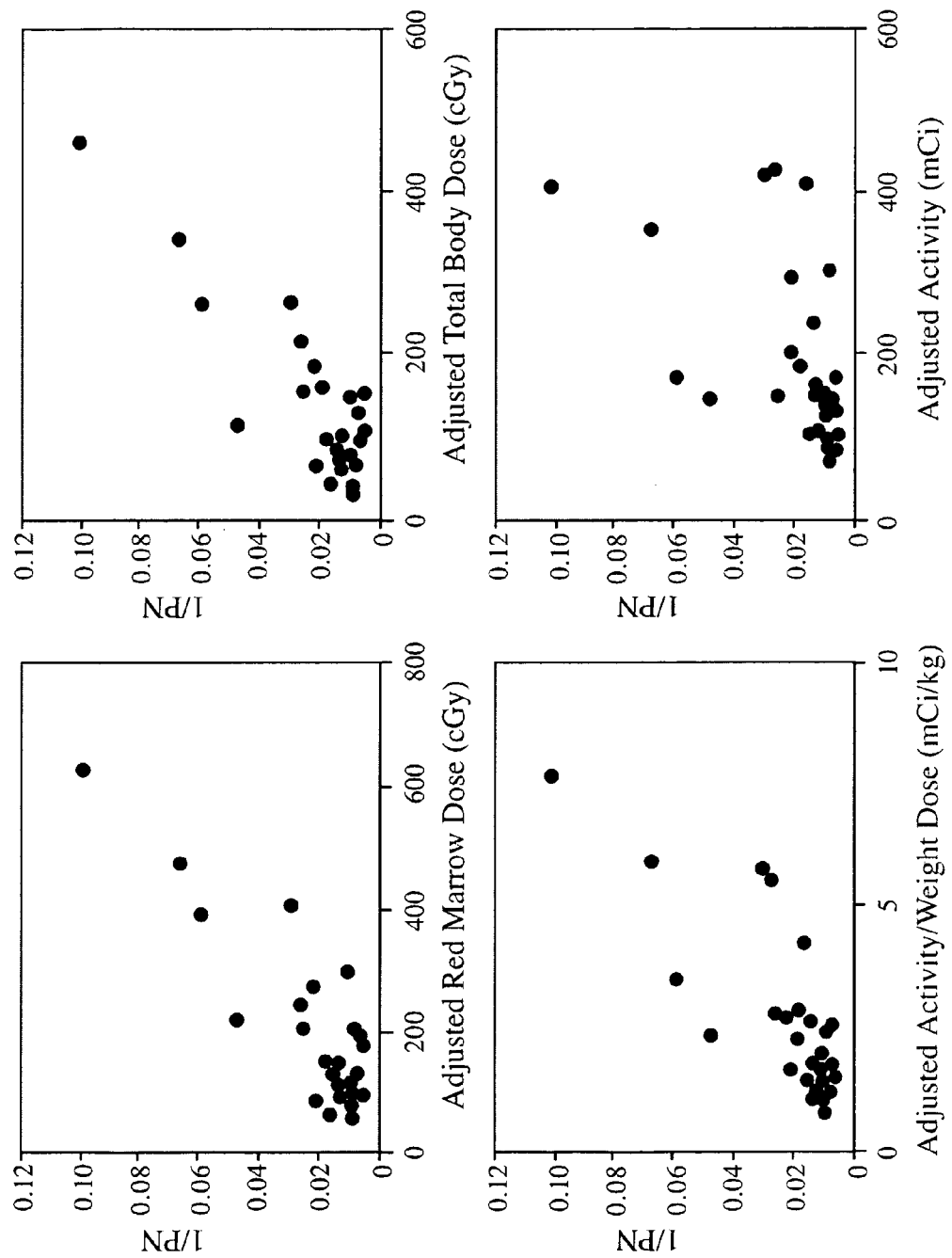
FIG. 5. Comparisons of 1/platelet nadir (PN) with FLT3-L adjusted predictors of toxicity.

The correlation coefficients for PN versus radiation dose were determined using an exponential function; all other correlations were determined using linear regression. The comparisons of PN with the FLT3-L adjusted predictors of toxicity are shown in FIG. 4, and the comparisons of 1/PN with the FLT3-L adjusted toxicity predictors are shown in FIG. 5.

Poor correlations were observed between the administered activity and PTG, PPD, PN and 1/PN (r=0.05, 0.15, 0.03 and 0.21, respectively) and the administered activity per unit body weight and these hematologic toxicity measures (r=0.28, 0.33, 0.18 and 0.04, respectively). Similar poor correlations were observed between red marrow radiation dose and PTG, PPD, PN and 1/PN (r=0.28, 0.15, 0.22, and 0.20, respectively). Correlations between FLT3-L-adjusted marrow dose and PTG, PPD, PN and 1/PN were greatly improved (r=0.70, 0.48, 0.76, and 0.86, respectively), as were the correlations for administered activity and administered activity per unit body weight. Correlations between FLT3-L-adjusted total body dose, using only the MIRDOSE 3 dosimetric model, and PTG, PPD, PN and 1/PN were 0.68, 0.46, 0.75, and 0.86, respectively.

Only 8 patients had a PTG of 3 or 4. RM dose adjusted for FLT3-L versus 1/PN for these patients resulted in a correlation coefficient of 0.85. FLT3-L-adjusted TB dose, administered activity and administered activity per unit body weight versus 1/PN resulted in correlation coefficients of 0.81, 0.14, and 0.60, respectively. The other 22 patients had grade 0-2 platelet toxicities; adjusted RM dose versus 1/PN for these patients resulted in a correlation coefficient of 0.18. Adjusted TB dose, administered activity and administered activity per unit body weight versus 1/PN resulted in correlation coefficients of 0.33, 0.42, and 0.27, respectively.

The FLT3-L-adjusted red marrow doses, using the male MIRDOSE 3 model, Equation 3 and a CF of 0.3, were compared to the FLT3-L-adjusted administered activities per unit body weights and unadjusted red marrow dose as predictors of Grade 3 or higher toxicity by determining sensitivity, specificity, accuracy, positive predictive value (PPV) and negative predictive value (NPV). Using a threshold value of 200 cGy for the adjusted red marrow dose, there were 8 true positives, 0 false negatives, 2 false positives and 20 true negatives, resulting in a sensitivity, specificity, accuracy, PPV, and NPV of 100%, 90.9%, 93.3%, 80%, and 100%, respectively. Although the number of patients with Grade 3 or higher hematologic toxicity was low (n=8), there were 22 patients who did not develop Grade 3 or higher toxicity, and in these patients there were no false negatives but 20 true negatives. Using a threshold value of 100 cGy for red marrow dose by itself, there were 8 true positives, 0 false negatives, 13 false positives and 9 true negatives, resulting in a sensitivity, specificity, accuracy, PPV, and NPV of 100%, 40.9%, 56.7%, 38.1%, and 100%, respectively. Using a threshold value of 74 MBq/kg for the adjusted activity per body weight, there were 8 true positives, 0 false negatives, 6 false positives, and 16 true negatives resulting, in a sensitivity, specificity, accuracy, PPV, and NPV of 100%, 72.7%, 80%, 57.1%, and 100%, respectively.

Correlations for dose-toxicity were as high as 0.86 between FLT3-L-adjusted radiation dose and the inverse of platelet nadir as the measure of hematologic toxicity. Correlations with this latter parameter were much higher compared to all other measures of hematologic toxicity (platelet toxicity grade, percent platelet decrease, and platelet nadir); the correlation coefficients jumped from a range of approximately 0.5-0.8 up to almost 0.9. The use of 1/PN appears to transform the PN-hematologic toxicity predictor curves to the anticipated shape of a dose-response curve (i.e., at low dose limited toxicity is observed followed by increasing toxicity at higher dose in a nonlinear fashion). The classic sigmoidal curve was not observed, presumably due to the fact that the calculated dose levels were not high enough to establish this shape. Thus, it is reasonable to expect that linear correlation with 1/PN versus the various predictors of toxicity would result in a much stronger correlation than the other toxicity measures.

In this limited patient population, clear distinctions were not found in the correlations between patients with long or short effective half-times in blood. This explains why the FLT3-L adjustment of total-body dose and administered activity per unit body weight correlated with observed toxicity as well as red marrow absorbed dose (the correlations involving administered activity were not as good). When patients were separated in terms of the severity of their bone marrow toxicity (i.e., Grade 3 or 4 platelet toxicity versus those patients with a PTG of 0-2), both red marrow and total-body dose resulted in stronger correlations than administered activity and administered activity per unit body weight. In addition, FLT3-L adjusted red marrow dose resulted in higher specificity, accuracy, and positive predictive value compared to adjusted activity per unit body weight and red marrow dose by itself. Furthermore, when using FLT3-L-adjusted red marrow dose as a predictor of hematologic toxicity, there were no false negatives and 20 of the 22 patients with less than Grade 3 toxicity were true negatives.

The blood-based red marrow dosimetry approaches in this study are justifiable since no patient had bone marrow and/or bone metastases and the radiolabeled monoclonal antibodies administered do not bind to any blood, marrow, or bone components, with one caveat. Patients who are recovering from chemotherapy may have hyperproliferating bone marrow with enhanced radioantibody uptake (Juweid M, Sharkey R M, Siegel J A, Behr T, Goldenberg D M. Estimates of red marrow dose by sacral scintigraphy in radioimmunotherapy patients having non-Hodgkin's lymphoma and diffuse bone marrow uptake. Cancer Res. 1995; 55 (suppl):5827s-5831 s). If such involvement were present, red marrow dosimetry would need to take this into consideration. In such patients image-based red marrow dose estimates have been shown to better predict myelotoxicity (Juweid M, Sharkey R M, Siegel J A, Behr T, Goldenberg D M. Estimates of red marrow dose by sacral scintigraphy in radioimmunotherapy patients having non-Hodgkin's lymphoma and diffuse bone marrow uptake. Cancer Res. 1995; 55 (suppl):5827s-5831s, Macey D J, DeNardo S J, DeNardo G L. Estimation of radiation absorbed doses to red marrow in radioimmunotherapy. Clin Nucl Med. 1995; 20:117-125). It has also recently been claimed that image-based red marrow dose estimates might improve the prediction of toxicity for non-marrow targeting $^{90}$Y antibody therapy (Shen S, Meredith R F, Duan J, Brezovich I A, Robert F, Lobuglio A F. Improved prediction of myelotoxicity using imaging dose estimate for non-marrow targeting $^{90}$Y-antibody therapy [abstract]. J Nucl Med. 2001; 5 (suppl): 22P).

CONCLUSION

FLT3-L adjusted red marrow and total-body radiation doses provide improved correlation with hematologic toxicity. The adjusted absorbed doses provided a stronger dose-toxicity correlation than the use of simpler empirical parameters, such as administered activity and administered activity per unit body weight. Elevated FLT3-L plasma levels prior to RAIT indicate increased radiosensitivity of the bone marrow, and use of this measurement to adjust calculated red marrow or total body radiation doses provides a significantly better prediction of toxicity than radiation dose alone, leading to better treatment planning and minimization of toxicity by optimization of administered activity. Improved methods for red marrow absorbed dose estimates will allow for even better treatment optimization. Further, in those patients identified to be at low risk for toxicity, the administered activity may be increased, potentially leading to a greater treatment benefit.

The foregoing detailed description and Examples are merely meant to be illustrative, and not limiting in any way. The artisan will immediately appreciate that there are other aspects falling within the invention that are not specifically exemplified. All references cited above are herein incorporated in their entirety to the same extent as if each was individually incorporated.

What is claimed is:

1. A method of determining a dose of G-CSF to be administered to a patient before or after a myelosuppressive agent is to be administered to the patient, comprising:
   (a) measuring a level of G-CSF in a sample from the patient;
   (b) comparing the level of G-CSF measured in the sample to levels of G-CSF in normal subjects;
   (c) determining the dose of G-CSF to be administered to the patient based on the comparison of G-CSF levels; and
   (d) administering the dose of G-CSF to the patient.

2. The method of claim 1 wherein the level of G-CSF is measured in the patient before administering the myelosuppressive agent to the patient.

3. The method of claim 1 wherein the level of G-CSF is measured in the patient after administering the myelosuppressive agent to the patient.

4. The method of claim 1 wherein the level of G-CSF is measured in the patient before and after administering the myelosuppressive agent to the patient.

5. The method of claim 1 further comprising measuring levels of at least one other hematopoietic cytokine selected from the group consisting of SCE, ELT-3L, JL-1, IL-3, IL-11, MIP-1α, TGF-γ3 and TNF-α in the sample.

* * * * *